United States Patent [19]

Mouradian et al.

[11] Patent Number: 5,737,238
[45] Date of Patent: Apr. 7, 1998

[54] METHOD AND APPARATUS FOR PLY DISCONTINUITY DETECTION

[75] Inventors: Dean C. Mouradian, West Allis, Wis.; Jim A. Michaud, Kettering; James T. Zalusky, Beavercreek, both of Ohio

[73] Assignee: Hyde Park Electronics, Inc., Dayton, Ohio

[21] Appl. No.: 703,951

[22] Filed: Aug. 28, 1996

[51] Int. Cl.⁶ .................................................. G06F 19/00
[52] U.S. Cl. ........................................ 364/507; 364/550
[58] Field of Search ........................ 364/468.16, 468.17, 364/507, 550

[56] References Cited

U.S. PATENT DOCUMENTS

| | | | |
|---|---|---|---|
| 3,409,779 | 11/1968 | Fertig | 364/507 X |
| 3,781,531 | 12/1973 | Baker | 364/507 |
| 3,970,857 | 7/1976 | Buckson | 250/559.1 |
| 4,389,893 | 6/1983 | Ophir et al. | 73/599 |
| 4,512,194 | 4/1985 | Beuter | 73/579 |
| 4,607,341 | 8/1986 | Monchalin | 364/557 |
| 4,621,645 | 11/1986 | Flax | 128/660 |
| 4,676,251 | 6/1987 | Bernatets | 128/660 |
| 5,261,280 | 11/1993 | Matzuk | 73/602 |
| 5,283,623 | 2/1994 | Muhlberg et al. | 356/238 |
| 5,303,590 | 4/1994 | Modderman et al. | 73/588 |
| 5,671,154 | 9/1997 | Lizuka et al. | 364/507 |
| 5,671,155 | 9/1997 | Edens et al. | 364/507 |

FOREIGN PATENT DOCUMENTS 2204690  11/1988  United Kingdom .

*Primary Examiner*—Edward R. Cosimano

[57] ABSTRACT

A ply break detector for a laminate web uses a short time constant low pass filter and a long time constant low pass filter for filtering output signals from a sonic web scanner. A difference circuit compares output signals from the two filters to create a difference signal. A ply discontinuity indication is generated when the difference signal exceeds a predetermined threshhold with a predetermined persistence. Analog and digital versions are disclosed.

26 Claims, 5 Drawing Sheets

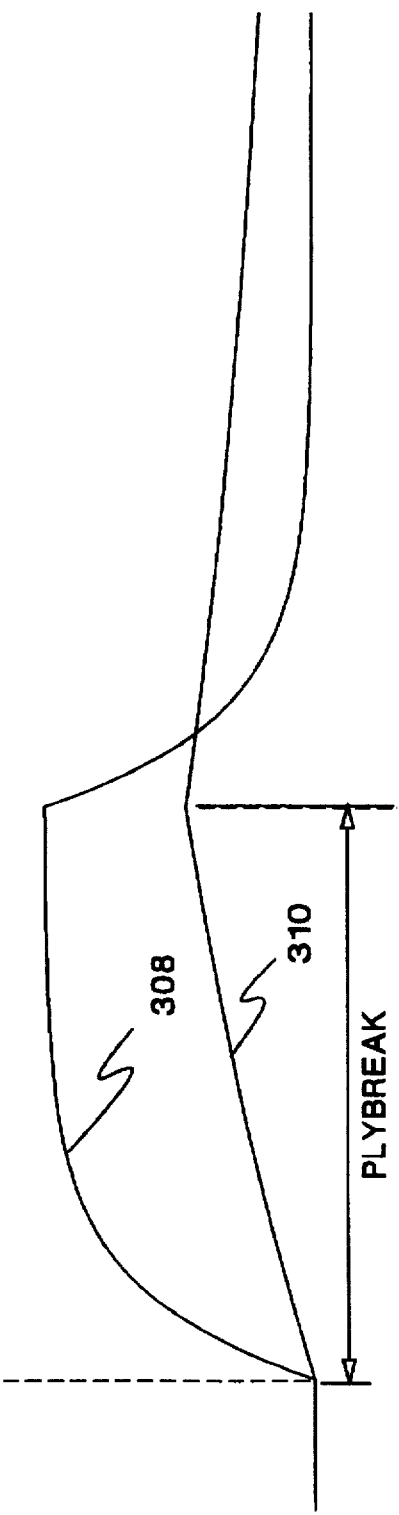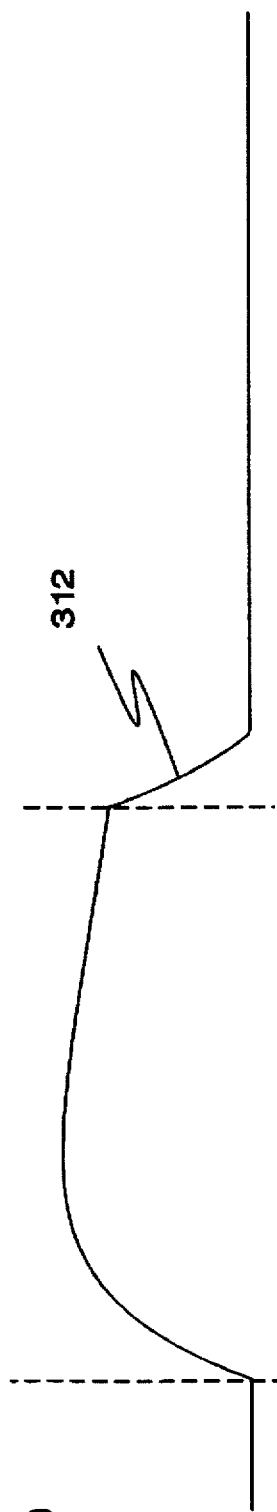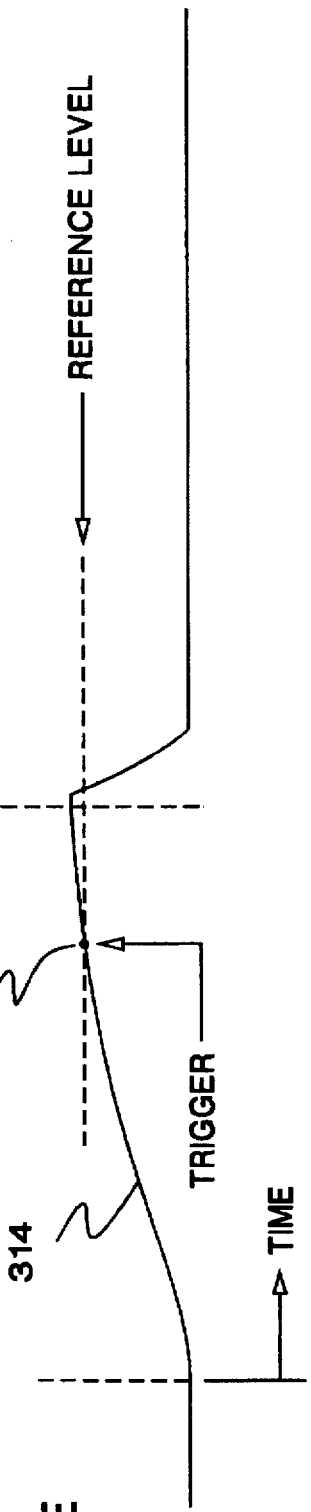

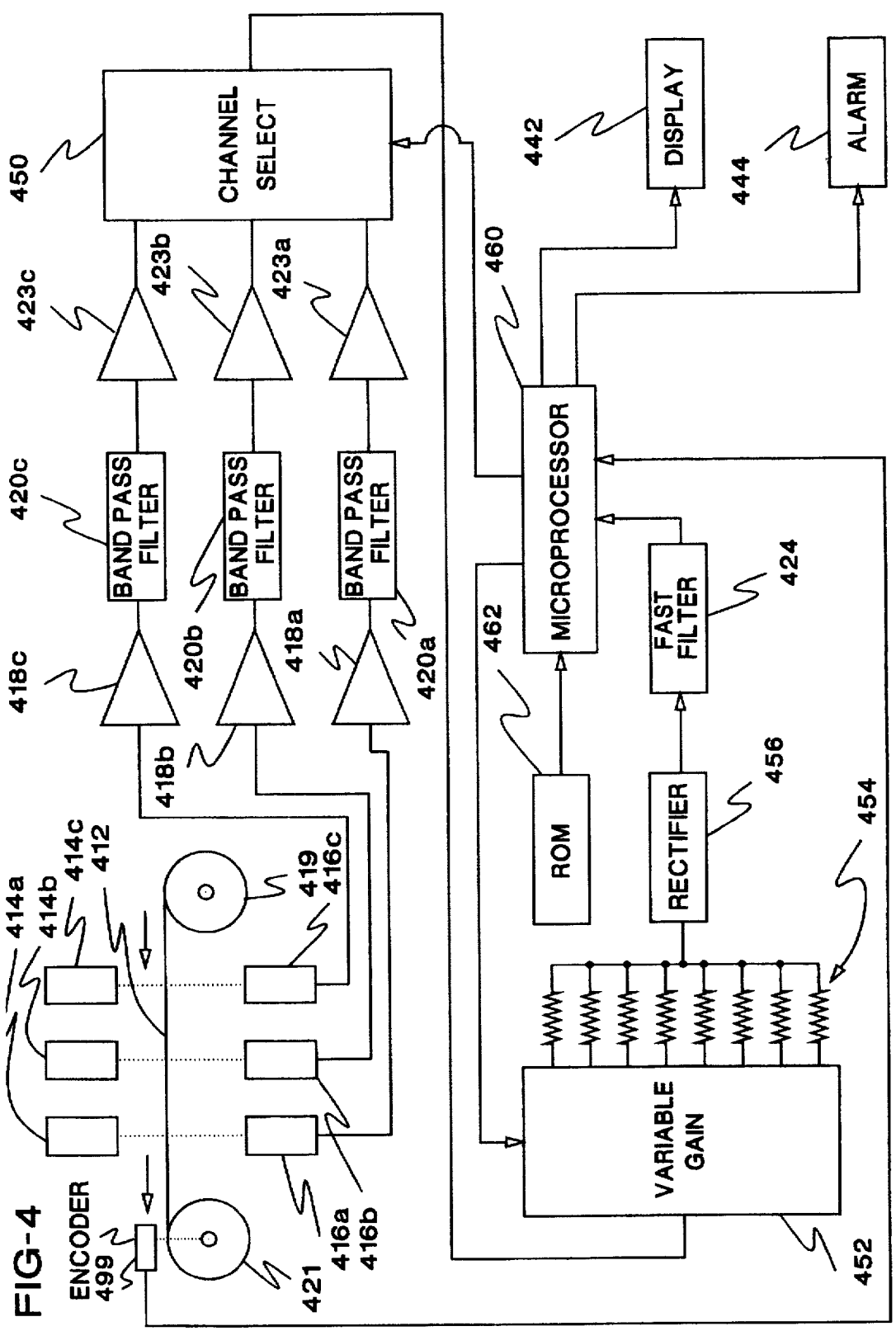

METHOD AND APPARATUS FOR PLY DISCONTINUITY DETECTION

BACKGROUND OF THE INVENTION

This invention relates to the field of inspection of webs of laminated material, such as paper products having a plurality of plies. It has particular application to web converting processes wherein a laminated paper web is fed to a printer. It often times happens that insignificant openings appear in the plies. In general such openings are not in registration with openings in other plies and are not cause for remedial action. Typically ply openings or "holes" may be as large as 1 inch in diameter without becoming objectionable. Larger ply openings should be detected and treated as ply breaks.

Prior art ply break detection systems have been generally unsatisfactory. The best performance has been obtained from sonic scanners which transmit beams of continuous wave sonic energy perpendicularly through the moving web for reception by a suitably positioned receiver. It has been found that there is a perceptible change in the level of the received signal when a ply opening passes through the sonic wave front. However, the signal amplitude differences are subtle and hard to quantify. And while a large area break may be recognized, there has been no practical and satisfactory of discriminating between a large hole and a small break or other discontinuity.

SUMMARY OF THE INVENTION

This invention solves the ply discontinuity detection problem by filtering and processing a beam of sonic energy which has been modulated by a laminated web. A sonic receiver receives the beam of sonic energy and creates two sample streams. The two sample streams are filtered by filters having different frequency response characteristics. The two filtered streams are compared to produce a difference signal representing a web discontinuity. The difference signal then is timed, and a ply discontinuity is declared if a predetermined difference has a predetermined persistence.

Preferably the system utilizes a continuous wave sonic transmitter which directs a beam of sonic energy through the web for reception by a receiver positioned opposite the transmitter. A band pass filter removes noise from the receive signal and relays a clean sensing signal to a rectifier. The rectifier produces a rectified signal which is filtered by a low pass filter having a relatively short time constant. This produces a first sample stream. The sensing signal is also filtered by a second low pass filter having a relatively long time constant.

In a first embodiment of the invention the second low pass filter is implemented in analog circuitry. A microprocessor performs the function of the second low pass filter in an alternative embodiment. Preferably the second low pass filter has a time constant ranging from 10–100 times the length of the time constant of the first low pass filter.

In the analog implementation of the invention the difference signal causes a current flow through the series combination of a timing capacitor and a resistor. There is also a reversed biased diode in parallel with the resistor, so that when the difference signal drops, the timing capacitor discharges rapidly through the diode. This means that the charge on the timing capacitor represents the time of persistence of the difference signal. A ply discontinuity is declared when and if the charge on the timing capacitor reaches some predetermined reference level.

In the alternative embodiment the microprocessor counts clock pulses and encoder pulses to obtain a persistence measure for a predetermined value of the difference signal.

Accordingly, it is an object of the present invention to provide a method and an apparatus for recognizing a ply discontinuity of a predetermined size in a web of laminated material.

Other objects and advantages of the invention will be apparent from the following description, the accompanying drawings and the appended claims.

BRIEF DESCRIPTION OF THE DRAWING

FIGS. 3B–3E illustrate signals which may be produced by the ply discontinuity detection system of FIG. 1 in the presence of the product of FIG. 3A.

FIG. 4 is a schematic illustration of a ply discontinuity detection system in an alternative embodiment.

DESCRIPTION OF THE PREFERRED EMBODIMENT

Figure 1:
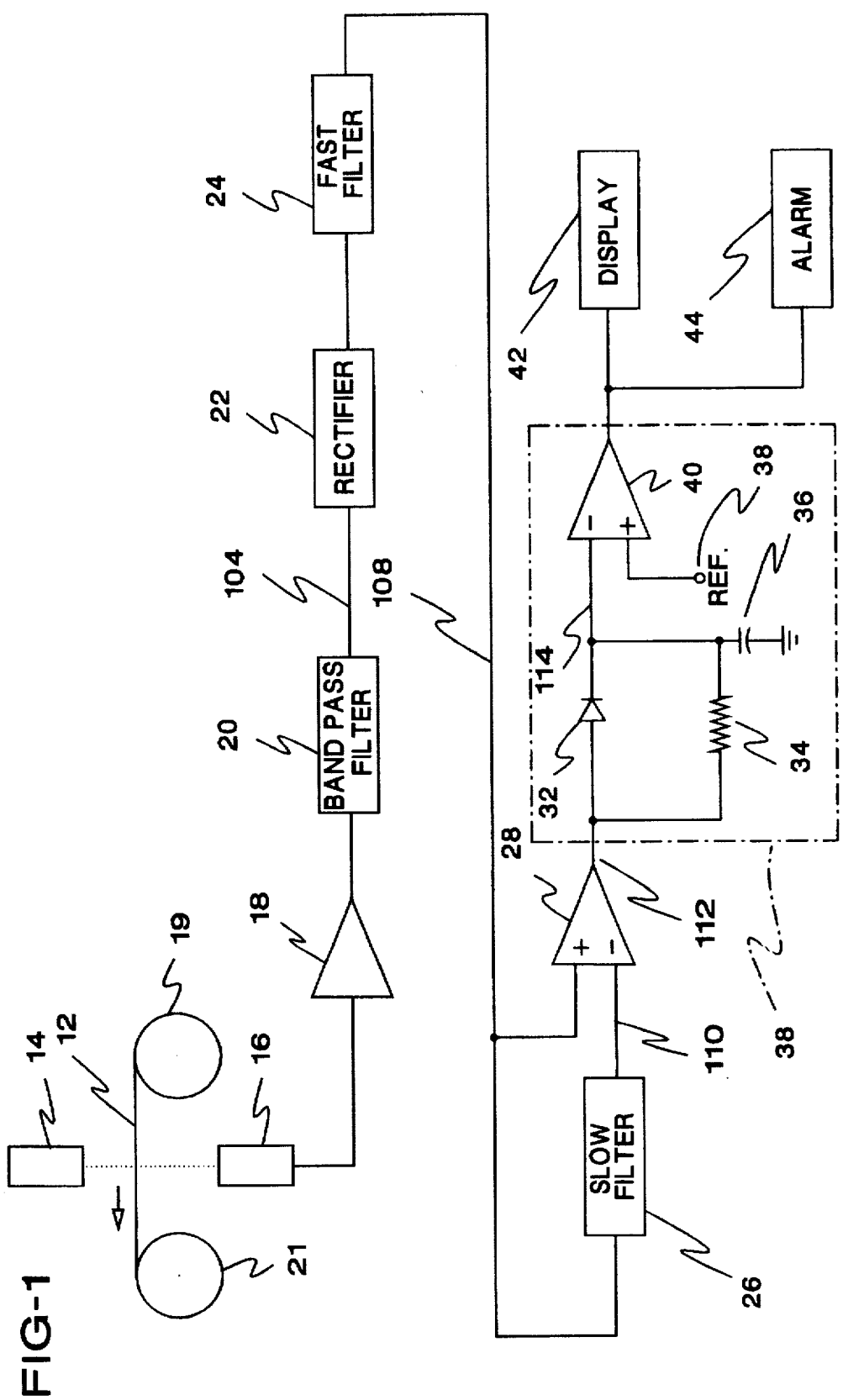
FIG. 1 is a schematic illustration of a ply discontinuity detection system in a first embodiment.

A preferred embodiment of the invention may be configured as generally illustrated in FIG. 1. Thus a web of laminated material 12 may be drawn between a pair of rolls 19, 21 beneath a sonic transmitter 14. Sonic transmitter 14 may transmit a beam of continuous wave sonic energy through web 12 and toward a receiver 16 at a frequency ranging between about 40 KHZ and 1 MHZ and typically about 180 KHZ. Receiver 16 generates a scanning signal which is amplified by an amplifier 18 and then directed to a band pass filter 20.

Figure 2A:
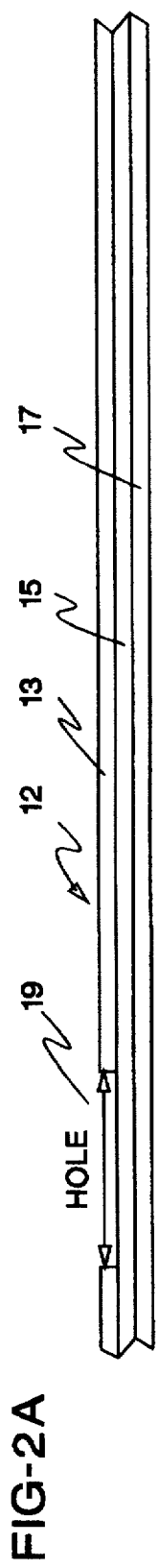
FIG. 2A is an illustration of a laminated product having a hole in a ply.
Figure 3A:
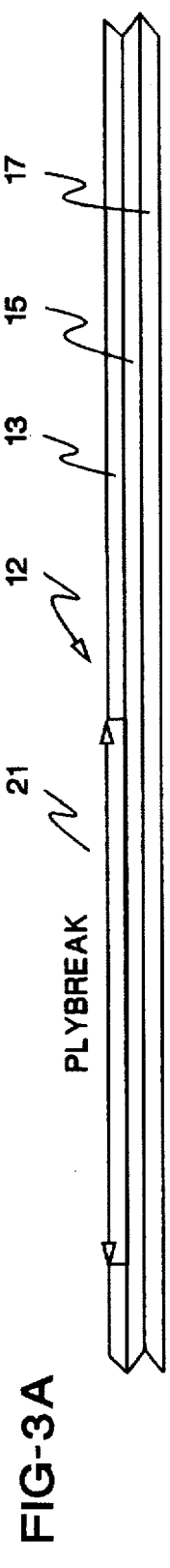
FIG. 3A is an illustration of a laminated product having a break in a ply.

Web 12 may appear as generally illustrated in either of FIGS. 2A or 3A. Thus web 12 may comprise a series of plies 13, 15, 17. The illustrated plies may all be perfectly continuous. From time to time one of the plies such as ply 13 may have a small discontinuity in the nature of a hole 19 as illustrated in FIG. 2A. Hole 19 may be of relatively minor size in the order of 1 inch in diameter or less. Occasionally, as illustrated in FIG. 3A there may be larger ply discontinuity 21 which may be termed a ply break. It will be appreciated that "ply break" is merely a term arbitrarily applied to ply discontinuities which are greater than some specified size. The dividing line between the hole and the break depends upon the nature of the product being produced. Thus if web 12 is being converted into high quality paper napkins to be used in banquets, then only extremely small holes may be tolerated. On the other hand, if web 12 is being converted into paper toweling for general use, then somewhat larger discontinuities may be tolerated. Thus a ply break is a discontinuity in a ply having a size larger than can be tolerated for the particular product being produced. When a ply break is detected, the system must be shut down for corrective action.

Figure 2B:
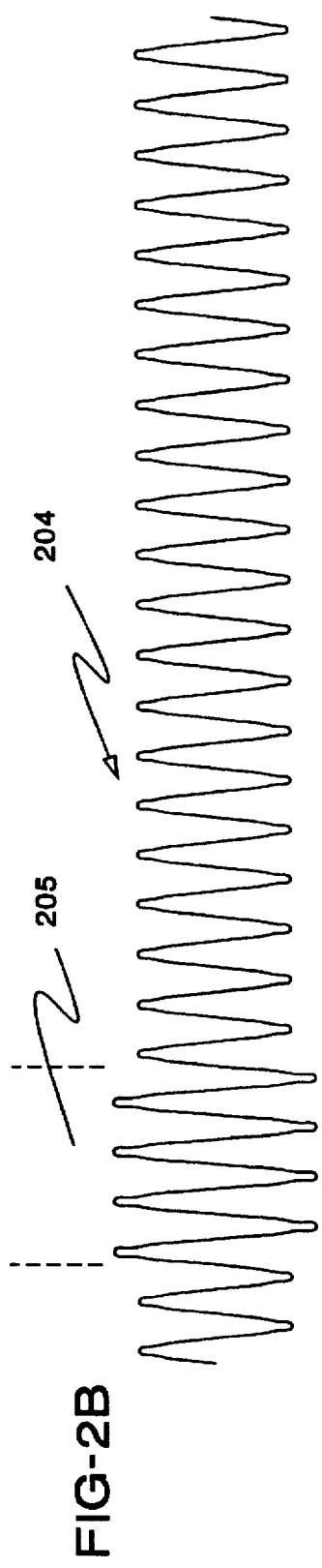
FIGS. 2B–2E illustrate signals which may be produced by the ply discontinuity detection system of FIG. 1 in the presence of the product of FIG. 2A.

Referring again to FIG. 1, band pass filter 20 passes a band of frequencies centered at 180 KHZ so as to produce a clean, noise free sensing signal on line 104 for transmission to rectifier 22. The signal on line 104 may appear as generally illustrated in either of FIGS. 2B or 3B. As illustrated in FIG. 2B, the signal on line 104 is indicated generally by the reference numeral 204 and has a generally sinusoidal shape. The amplitude of the sinusoid increases in the presence of hole 19 as generally illustrated in FIG. 2B by the reference numeral 205. It will be appreciated that the representation of signal 204 is highly schematic for purposes of illustration. A true representation would show the sign wave at a much higher frequency, so that the sign waves would become bunched together into a series of side by side vertical line segments.

Figure 3B:
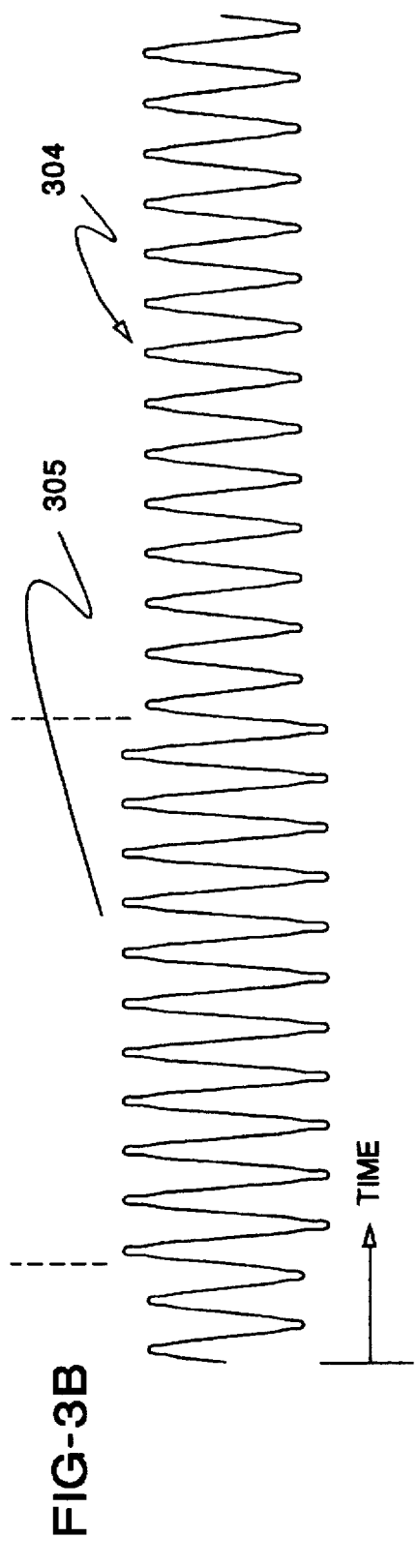

The corresponding sensing signal in the presence of a ply break 21 is indicated in FIG. 3B by the reference numeral 304. As therein illustrated the ply break 21 is indicated by a wave portion 305 of increased amplitude.

The sensing signal, as illustrated in either of FIGS. 2B or 3B is rectified by rectifier 22 and then applied to a fast filter 24. Fast filter 24 is a low pass filter with a time constant short enough to pass the fundamental frequency of a hole 19 but long enough to remove the 180 KHZ carrier frequency. This produces a first sample stream which is applied to output line 108 from fast filter 24. That signal may appear as generally illustrated by reference numeral 208 of FIG. 2C or reference numeral 308 of FIG. 3C, again depending upon the condition of web 12.

Figure 2C:
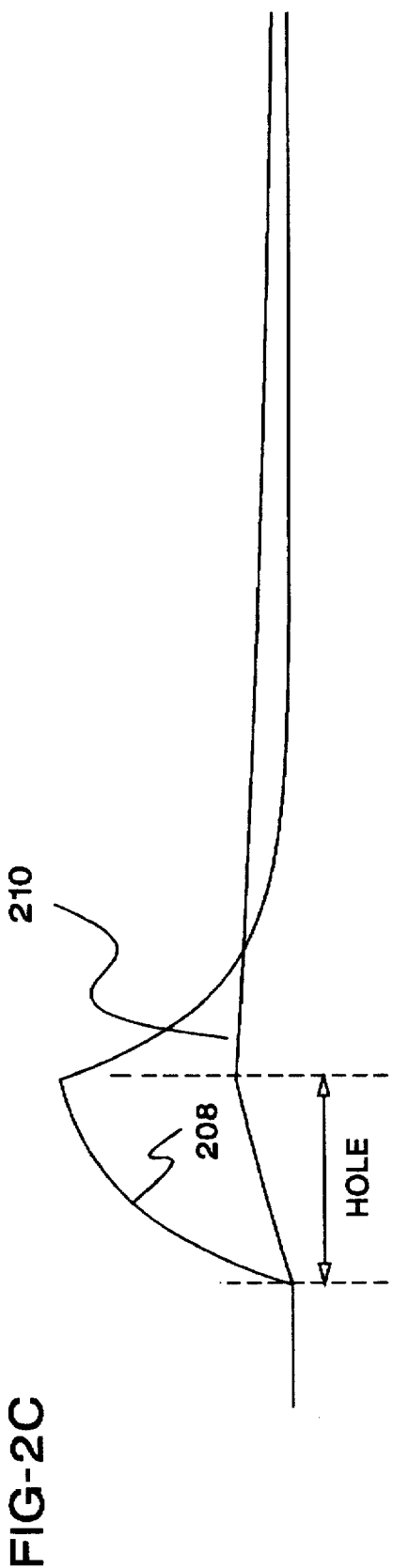
Figure 2D:

As further shown in FIG. 1, the first sample stream 208 or 308 is directed to slow filter 26 and also to a differential amplifier 28. Slow filter 26 is a low pass filter having a longer time constant than fast filter 24. It is a mere matter of choice and convenience that the output from fast filter 24 is applied to slow filter 26. Alternatively, the output from rectifier 22 may be split, so that fast filter 24 and slow filter 26 operate in parallel. Either way slow filter 26 discriminates against high frequency phenomena and generates a second sample stream 210 (as illustrated in FIG. 2C) or 310 (as illustrated in FIG. 3C) on line 110 for application to differential amplifier 28. Differential amplifier 28 subtracts the first sample stream from the second sample stream to produce a difference signal on line 112. This difference signal may have wave form 212 as shown in FIG. 2D or wave form 312 as shown in FIG. 3D. It is a feature of this invention that a ply discontinuity is declared when the difference signal, 212 or 312, has a predetermined value which exhibits a predetermined persistence, as discussed in detail below. That determination is made for the embodiment of FIG. 1 by an ON-DELAY circuit 38.

ON-DELAY circuit 38 may comprise a parallel combination of a diode 32 and a resistor 34 connected to line 112 for reception of difference signal 212, or 312. When the second sample signal on line 110 exceeds the first sample signal on line 108, diode 32 is reverse biased, so that the output from differential amplifier 28 flows through resistor 34 to one side of a timing capacitor 36. The other side of timing capacitor 36 is connected to ground.

Figure 2E:
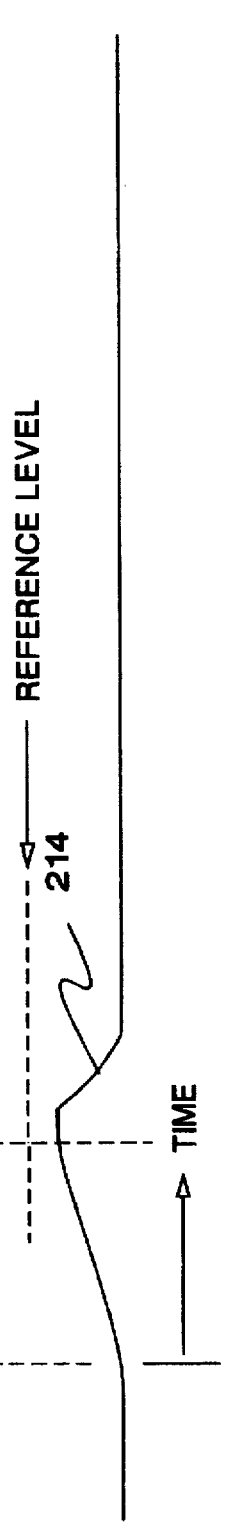

Differential amplifier 112 cannot go negative at its output, so that when the first sample stream has a value which exceeds that of the second sample stream, the difference signal, 212 or 312 simply goes to zero. However, as the difference signal begins failing in amplitude, timing capacitor 36 discharges rapidly through diode 32. The voltage across timing capacitor 36 therefore appears as illustrated by line 214 of FIG. 2E or line 314 of FIG. 3E. This signal is applied to the negative input terminal of a differential amplifier 40. A source of reference potential is applied to a terminal 38 connected to the positive input terminal of differential amplifier 40. Whenever the voltage across timing capacitor 36 exceeds the reference voltage on terminal 38, differential amplifier 40 produces a ply break indication which is transmitted to a display 42 and also to an alarm 44.

Due to the relatively small size of the hole 19, the build up of difference signal 212 is relatively short in time, and the signal on line 214 never reaches the reference voltage at terminal 38. However, in the case of a ply break, as illustrated in FIGS. 3C-3E, the signal 314 on line 114 continues rising to a trigger point 315. Differential amplifier 40 may be configured for triggering when the signal on line 114 reaches about 10.1 volts and remaining triggered until the signal on line 114 drops to 9.4 volts. This prevents chattering in the output of ON-DELAY circuit 38.

Referring now to FIG. 4 the operation of an alternative embodiment will be described. In general the operation of the embodiment of FIG. 4 is quite similar to that of the embodiment of FIG. 1, except that there are a plurality of sonic input channels, and the functions of slow filter 26 and ON-DELAY circuit 38 have been implemented inside a microprocessor 460. As shown in FIG. 4 there may be a plurality of sonic transmitters such as sonic transmitters 414A, 414B and 414C transmitting a plurality of sonic beams through a laminated web 412 to a plurality of sonic receivers 416A, 416B, 416C. Web 412 may be transported through the paths of the sonic beams by rollers 419, 421. FIG. 4 illustrates the transmitters and receivers as being arranged in tandem along the web, whereas in reality the preferred arrangement would be transverse. Preferably there is an encoder 499 which monitors web movement and generates corresponding distance pulses for use as described below.

Sonic receivers 416A, 416B, 416C generate three scanning signals which are applied to amplifiers 418A–418C. The three scanning signals then are processed by band pass filters 420A–420C and amplifiers 423A–423C for application to a channel select unit 450. Channel select unit 450 is merely an analog switch which operates under control of microprocessor 460 to select and monitor the three scanning signals on a repeating basis. Selection is performed sequentially at a sufficiently high frequency that the system effectively performs parallel monitoring of ply conditions at three spaced positions across web 412. In general it is desirable to adjust the gain of the system for best performance. When a plurality of sonic transducers are employed, slight manufacturing differences may call for slightly different system gains. Such adjustment is accomplished by means of an array of resistors 454 arranged in parallel at the output of a variable gain unit 452. Variable gain unit 452 is an analog switch which takes the output from channel select unit 450 and switches it into communication with rectifier 456 via an appropriate voltage dropping resistor. The resistors in array 454 all have different resistances, and microprocessor 460 is programmed to select those resistances in synchronism with channel selection in accordance with previously determined set up information.

The sensing signals are rectified by rectifier 456 and then are applied to fast filter 424 which corresponds to fast filter 24 of FIG. 1. Fast filter 424 produces a first sample stream (in reality 3 multiplexed first sample streams) to microprocessor 460 which operates under control of a program stored in a ROM 462 for performing the functions of slow filter 26, differential amplifier 28 and ON-DELAY unit 38. Microprocessor 460 operates in accordance with that program to provide appropriate driving signals for a display 442 and an alarm 444. Microprocessor 460 is interchangeable with the analog components which it replaces. However, due to the incremental, discrete nature of digital processing, the digital counterparts of lines 210, 310 may take on a stepped appearance, and lines 212, 312 may not be quite as smooth as the illustrations of FIGS. 2D, 3D. Furthermore, there is no timing capacitor and therefore no signal corresponding to signals 214, 314 of FIGS. 2E, 3E. There is, instead, an exact measurement of the difference between the two sample streams and an exact measurement of the time and distance of persistence of any particular signal condition.

It may be shown that for simple first order filters the signal on line 112 is given by the expression:

$$R = EXP(-T/M/P)*(1-EXP(1/M)) - EXP(-T/N/P)*(1-EXP(1/N))$$

Where:

R is the ratio of signal difference divided by maximum steady state signal deviation P is the dwell time of a discontinuity in a ply T is the ratio of observation time to P M is ratio of slow time constant to P N is the ratio of fast time constant to P This equation may be solved iteratively to produce criteria for declaration of a ply discontinuity. The results of a series of such calculations are presented in Table 1 below.

TABLE I

| R | M | N | T |
|---|---|---|---|
| 0 | 200 | 2 | 9.9 |
| .2 | 200 | 2 | 2.4 |
| .35 | 200 | 2 | 1.2 |
| .2 | 10 | 1 | 1.8 |
| 0 | 5 | .5 | 1.9 |
| .2 | 100 | 1 | 2.1 |

Assume, for example, that a system according to this invention inspects a web traveling at 240 in. per sec. and that a ply break is to be declared for discontinuities in excess of 1 inch in the direction of travel. The dwell time for such a discontinuity is 0.0042 sec. Further assume that M is 200 and N is 2. Then a predetermined difference ratio of 0.2 will persist for 2.4 dwell periods. This means that a timing cycle should be initiated when a difference is detected between the output signals from fast filter 24 and slow filter 26 and that a ply break should be declared if the difference ratio is at least 0.2 at the end of 10 millisec. It will be appreciated that a voltage value miry be assigned to R prior to setup by routine inspection of test webs having continuous plies and broken plies. It will be further appreciated that selection of values for M and N involves a good deal of compromise. It has been found, however that value of 2 is nearly ideal for N. Preferably, M should be 10 to 100 times N. The higher values are most preferred but create implementation problems when digital filtering is employed.

In an analog implementation, as illustrated in FIG. 1, Fast Filter 22 may have a fixed time constant in the order of about 1 millisec., and Slow Filter 26 may include a variable resistor (not illustrated) for providing an adjustable time constant ranging between about 10 and 100 millisec. Resistor 34 may have a resistance in the order of about 47K, and capacitor 36 may have a capacitance of about 10 microfarads.

For a digital implementation, as illustrated in FIG. 4, the functions of Slow Filter 26, Differential Amplifier 28 and ON-DELAY Circuit 38 may be provided by a program stored in appropriate software or firmware. The program operates under control of clock pulses and encoder pulses which occur at regular time and and web distance intervals. It also requires values for certain program constants as follows:

Speed_Low Minimum Speed for Filter Shifting

Ct_2_Max Spatial Count for Discontinuity Evaluation

Ct_5_Max Time Count For Discontinuity Evaluation

Threshold Difference Value Defining a Ply Discontinuity

The preferred digital filter stores and shifts 16 Difference values. So long as a defined value of Threshold is not exceeded, and the web speed is above Speed_Low, then the digital filter is caused to shift in response to timing pulses and to distance pulses. Due to the combined effect of the timing pulses and the distance pulses the filter time constant is approximately equal to 10 divided by the sum of the encoder frequency and the timer frequency. Speed_Low may have a value of about 10 inches per second. Values for the other parameters may be established in a straight forward manner, once the above discussed ratios R, P, T, M and N have been determined. Of course it is also necessary to measure the maximum steady state signal deviation for a web break and to know the frequency of the timing signal. A typical value of Ct_2_Max may be about 40.

Efficient operation is best achieved if the source code is written in assembler. However higher level languages may be used. For ease of understanding and by way of example, TABLES II–IV present source code for three interactive routines written in MICROSOFT VISUAL BASIC 4.00. This code is duplicated for each of the three channels.

TABLE II is a listing for an event driven Sub procedure named Encoder which is executed automatically upon generation of encoder pulses by encoder 499. In very general terms this Sub procedure counts distance intervals for which Threshold is exceeded (as indicated by a True value for Flag_1). If the number of such intervals is at least 75% of Ct_2$_{13}$ Max consecutive intervals, then a distance warning flag (Flag_2) is set True. If the Sub procedure of Table III has also set a time warning flag (Flag_3), then a ply discontinuity alarm is activated. The requirement for joint distance-dependent and time-dependent warnings greatly reduces susceptibility to environmental noise. It will be appreciated that noise can also cause a false negative. That is, a noise spike may mask a difference value in excess of Threshold. The Sub procedure allows for this by permitting up to 25% false negatives in Ct_2_consecutive intervals.

TABLE III is a listing for a Sub procedure called Timer_1 Timer which is executed automatically in response to timer pulses occurring at intervals of about 100 milliseconds. This procedure sets Flag_3 True when filtered ultrasonic signal differences exceed Threshold for at least 75% of Ct_5_ Max consecutive time intervals, again allowing 25% false negatives. The procedure initiates a ply discontinuity alarm, if it is called upon to raise Flag_3 at a time while Flag_2 also happens to be raised.

The digital filter Sub procedure may include code along the lines of the listing appearing in TABLE IV under the name "Signal". This Sub procedure is called by Encoder and by Timer_1 Timer each time either one is executed. Upon being called, Signal causes a function named Receiver to read the current value of the received ultrasonic signal and to return it in a variable called Signal_1. Then if Signal_1 differs from a filtered signal value, Signal_2, by more than Threshold, a warning flag, Flag_1, is set True, otherwise Flag_1 is set to False. If Flag_1 is False and the webspeed is above Speed_Low, then the signal values stored in the digital filter are all shifted up one position, and the current value of Signal_1 is placed at the end.. As this is being accomplished, a new filtered signal value is calculated.

TABLE II

```
Private Sub Encoder()
'Encoder Pulses Cause System Interrupts Which Call This Sub
'Called For Each Six Inches Of Web Travel
Call Get_Speed
'Get_Speed Calculates Web Speed By Reading The System Clock Count
'At Low Speed The Digital Filter Stops Working
Count_2 = Count_2 + 1
Call Signal
IfFlag_1 = True Then
        Count_3 = Count 3 + 1
        End If
IfCount_2 = Ct_2_MaxThen
        If 4 * Count_3 > 3 * Count_2 Then
                Flag_2 = True
                If Flag_3 = True Then
                        Call Alarm
                        End If
        Else
                Flag_2 = False
                End If
        Count_2 = 0
        Count_3 = 0
        End If
End Sub
```

TABLE III

```
Private Sub Timer_1Timer()
'Called Every 100 Milliseconds By System Clock
Call Signal
Count_5 = Count_5 + 1
IfFlag_1 = True Then
        Count_6 = Count_6 + 1
        End If
IfCount_5 = Ct_5_MaxThen
        If 4 * Count_6 > 3 * Count_5 Then
                Flag_3 = True
                If Flag_2 = True Then
                        Call Alarm
                        End If
        Else
                Flag_3 = False
                End If
        Count_5 = 0
        Count_6 = 0
        End If
End Sub
```

TABLE IV

```
Private Sub Signal()
'This Is The Digital Filter & Threshold Checker
'Initialize Filter
If Begin = True Then
        i = i + 1
        Signal_1 = Receiver
        X(16 - i) = Signal_1
        Sum = Sum + Signal_1
        If i = 16 Then
                Begin = False
                Average = Sum/ 16
                Signal_2 = (X(0) - Average)/Scale_Factor + Average
                i = 0
                End If
Else
        'Threshold Check
        If Signal_1 - Signal_2 > Threshold Then
                Flag_1 = True
        Else
                Flag_1 = False
                End If
        If(Speed => Speed_Low) And (Flag_1 = False) Then
                'Perform The Filtering
                Sum = 0
```

TABLE IV-continued

```
                'Shift Old Values
                For i = 15 To 1 Step-1
                        X(i) = X(i - 1)
                        Sum = Sum + X(i)
                        Next I
                'Get Current Value
                Signal_1 = Receiver
                X(0) = Signal_1
                Sum = Sum + X(0)
                Average = Sum/ 16
                'Calculate Filtered Value
                Signal_2 = (X(0) - Average)/Scale_Factor + Average
                End If
        End If
End Sub
```

While the forms of apparatus herein described and the methods of operation thereof constitute preferred embodiments of the invention, it is to be understood that the invention is not limited to these precise forms of apparatus or methods of operation, and that changes may be made in either without departing from the scope of the invention which is defined in the appended claims.

What is claimed is:

1. A method of detecting a ply discontinuity in a web of laminated material, said method comprising the steps of:

(1) Scanning said web by a beam of sonic energy, (2) Receiving said beam following said scanning and generating therefrom a first sample stream and a second sample stream, (3) Filtering said first sample stream to cause said first sample stream to differ from said second sample stream in a time dependent manner, (4) determining a difference between said first sample stream and said second sample stream, (5) Establishing a persistence measure for a predetermined value of said difference, and (6) Using said persistence measure to activate an alarm.

2. A method according to claim 1 wherein said scanning step directs a beam of continuous wave sonic energy along a path extending through said web, said scanning and said receiving being performed on opposite sides of said web.

3. A method according to claim 2 wherein said first sample stream is filtered by low pass filtering at a first cutoff frequency.

4. A method according to claim 3 further comprising the step of low pass filtering said second sample stream at a second cutoff frequency substantially lower than said first cutoff frequency.

5. A method of inspecting a moving web of laminated material comprising the steps of:

(1) Directing a beam of sonic energy at a predetermined frequency through said web, (2) Receiving said beam after passage through said web and generating a sensing signal which alternates at a base frequency corresponding to said predetermined frequency and has a modulation envelope corresponding to structural variations in said web, (3) Filtering said sensing signal to remove noise components therefrom, (4) Generating a first sample stream by low pass filtering said sensing signal with a first filtration time constant sufficiently long to remove said base frequency and sufficiently short to respond to discontinuities in said web, (5) Generating a second sample stream by filtering said sensing signal with a second filtration time constant different than said first filtration time constant, (6) Comparing said second sample stream with said first sample stream to determine a difference therebetween, and (7) Generating a ply discontinuity indication when said difference exceeds a predetermined amount with a predetermined persistence.

6. A method according to claim 5 wherein said second filtration time constant has a length approximately 10 to 100 times the length of said first filtration time constant.

7. A method according to claim 5 wherein said predetermined frequency is approximately 180 KHz.

8. A method according to claim 5 wherein a ply discontinuity indication is generated when said difference exceeds said predetermined amount for a predetermined period of time.

9. A method according to claim 5 wherein a ply break indication is generated when said difference exceeds said predetermined amount for a predetermined fraction of a predetermined period of time.

10. A method according to claim 5 further comprising the step of measuring a series of positions of said web, said ply break indication being generated when said difference exceeds said predetermined amount for a predetermined percentage of a predetermined number of consecutive positions of said web.

11. A method according to claim 10 wherein said predetermined percentage is approximately 75%.

12. Apparatus for detecting a ply break in a web of laminated material comprising:

(a) A sonic transmitter for directing a beam of sonic energy at said web, (b) A sonic receiver for receiving said beam of sonic energy from said web and generating a corresponding sensing signal, (c) A fast low pass filter having a first filtration time constant for generating a first sample stream by filtering said sensing signal, (d) A second low pass filter having a second filtration time constant substantiallly longer than said first filtration time constant for generating a second sample stream by filtering said sensing signal, (e) Comparing means for comparing said first sample stream and said second sample stream and generating a difference signal corresponding to a difference therebetween, and (f) On-Delay means for generating a ply break indicating signal when said difference signal exceeds a predetermined threshold for a predetermined period of time.

13. Apparatus according to claim 12 wherein said sonic transmitter and said sonic receiver are positioned on opposite sides of said web in mutually facing orientation.

14. Apparatus according to claim 13 wherein said sonic transmitter generates continuous wave sonic energy.

15. Apparatus according to claim 13 wherein said sonic transmitter generates continuous wave sonic energy at a frequency of approximately 180 KHz.

16. Apparatus according to claim 12 further comprising a band pass filter connected between said sonic receiver and said fast low pass filter for removing noise from said sensing signal.

17. Apparatus according to claim 16 further comprising a rectifier connected between said band pass filter and said first low pass filter for rectifying said sensing signal.

18. Apparatus according to claim 17 wherein said second low pass filter is in series with said first low pass filter.

19. Apparatus according to claim 18 wherein said comparing means comprises a first differential amplifier having a first input terminal connected for receiving said first sample stream, a second input terminal connected for receiving said second sample stream and an output terminal connected for delivering said difference signal to said On-Delay means.

20. Apparatus according to claim 19 wherein said On-Delay means comprises: a second differential amplifier having a third input terminal and a fourth input terminal, a source of reference potential connected to said fourth input terminal, a diode connected between said output terminal and said third input terminal, a resistor connected in parallel with said diode, a ground terminal and a timing capacitor connected between said ground terminal and said third input terminal.

21. Apparatus according to claim 20 further comprising an amplifier connected between said sonic receiver and said band pass filter.

22. Apparatus for detecting a ply break in a web of laminated material comprising:

(a) A plurality of sonic transmitters for directing a plurality of beams of sonic energy through said web, (b) A plurality of sonic receivers for receiving said beams of sonic energy after passage through said web and generating a plurality of corresponding sensing signals, (c) Channel select means including a plurality of channel input terminals connected for receiving said plurality of sensing signals, a selection output terminal and a switching control terminal, said channel select means being responsive to switching control signals on said switching control terminal for selectively connecting said selection output terminal to said channel input terminals, (d) A low pass filter connected for receiving a selected one of said sensing signals and having a first filtration time constant for generating a first sample stream by filtering said sensing signal, and (e) Digital computing means connected for receiving said first sample stream and organized for generating a second sample stream by digitally filtering said first sample stream with a second filtration time constant substantially longer than said first filtration time constant, said digital computing means being further organized for generating said switching control signals, generating a difference signal by comparing said second sample stream with said first sample stream and generating a ply break indicating signal when said difference signal exceeds a predetermined threshold with a predetermined persistence.

23. Apparatus according to claim 22 further comprising selectively adjustable amplifying means responsive to said microprocessor for amplifying said sensing signals in accordance with gain characteristics of sonic transmitters and sonic receivers switched into connection with said selection output terminal.

24. Apparatus according to claim 22 further comprising an encoder for generating a position signal indicating a series of positions of said web, said digital computing means being connected for receiving said position signal and and being programmed for establishing said persistence with reference to said positions.

25. A method of signalling a discontinuity in a travelling web comprising the steps of:

(1) Placing a plurality of ultrasonic transmitters at spaced widthwise positions across said web, (2) Causing said ultrasonic transmitters to direct beams of sonic energy into said web, (3) Thereafter generating a plurality of energy level signals by sensing said beams, (4) Generating a series of current sample values for each of said energy level signals by sampling said energy level signals in synchronism with movement of said web and also at regularly timed intervals, (5) Generating processed values of said energy level signals by digitally processing each said series of current sample values, (6) Comparing said current sample values against said processed values to obtain difference values, (7) Generating discontinuity indications when said difference values exceed a predetermined threshold, (8) Establishing a first warning condition when a first predetermined number of said discontinuity indications occur during a predetermined movement of said web, (9) Establishing a second warning condition when a second predetermined number of said discontinuity indications occur during a predetermined period of time, and

(10) Establishing an alarm condition when said first warning condition and said second warning condition co-exist.

26. A method according to claim 25 wherin said processed values are generated by a weighted averaging of previously generated current sample values.

* * * * *